United States Patent
Yoshiki et al.

(10) Patent No.: US 7,323,312 B2
(45) Date of Patent: Jan. 29, 2008

(54) TUMOR MARKER FOR UROTHELIAL CARCINOMA

(75) Inventors: Tatsuhiro Yoshiki, Shiga (JP); Susumu Kageyama, Kyoto (JP)

(73) Assignee: TSS Biotech Inc., Tokyo (JP)

( * ) Notice: Subject to any disclaimer, the term of this patent is extended or adjusted under 35 U.S.C. 154(b) by 0 days.

(21) Appl. No.: 10/482,188

(22) PCT Filed: Oct. 31, 2003

(86) PCT No.: PCT/JP03/14016

§ 371 (c)(1),
(2), (4) Date: Dec. 24, 2003

(87) PCT Pub. No.: WO2004/040313

PCT Pub. Date: May 13, 2004

(65) Prior Publication Data

US 2004/0248217 A1    Dec. 9, 2004

(30) Foreign Application Priority Data

Nov. 1, 2002    (JP) ............................. 2002-320355

(51) Int. Cl.
*G01N 33/53* (2006.01)
*G01N 33/574* (2006.01)
*C12Q 1/00* (2006.01)

(52) U.S. Cl. .......................... 435/7.1; 435/4; 435/7.23

(58) Field of Classification Search ................ 435/7.1, 435/7.23
See application file for complete search history.

(56) References Cited

U.S. PATENT DOCUMENTS 6,596,690 B2    7/2003 Tosato et al.
2003/0039970 A1    2/2003 Wang et al.

FOREIGN PATENT DOCUMENTS

WO    WO 00/20577 A1    4/2000
WO    WO 02/06327 A2    1/2002

OTHER PUBLICATIONS

Karl-Heinz Krause and Marek Michalak, Calreticulin Cell, vol. 88, 439-443, Feb. 21, 1997, Copyright.*

Marek Michalak 1, Elaine F. Corbett, Nasrin Mesaeli, Kimitoshi Nakamura and Michal Opas Calreticulin : one protein, one gene, many functions, Biochem. J. (1999) 344, 281±292 (.*
Alaiya A, Roblick U, Egevad L, Carlsson A, Franzen B, Volz D, Huwendiek S, Linder S, Auer GPolypeptide expression in prostate hyperplasia and prostate adenocarcinoma. Anal Cell Pathol. 2000;21(1):1-9.*
Ghil-Suk Yoon, Hojung Lee, Yusun Jung, Eunsil Yu, Hee-Bom Moon, Kyuyoung Song, and Inchul Lee, Nuclear Matrix of Calreticulin in Hepatocellular Carcinoma. Cancer Research 60, 1117-1120, Feb. 15, 2000.*
Conway EM, Liu L, Nowakowski B, Steiner-Mosonyi M, Ribeiro SP, Michalak M Heat shock-sensitive expression of calreticulin. In vitro and in vivo up-regulation. J. Biol Chem. Jul. 14, 1995;270(28):17011-6.*
Tockman MS, Gupta Pk, Pressman NJ, Mulshine JL. Considerations in bringing a cancer biomarker to clinical application. Cancer Res. May 1, 1992;52(9 Suppl):2711s-2718s.*
Pannek J, Rittenhouse HG, Evans CL, Finlay JA, Bruzek DJ, Cox JL, Chan DW, Subong EN, Partin AW, Molecular forms of prostate-specific antigen and human kallikrein 2 (hK2) in urine are not clinically useful for early detection . . . Urology. Nov. 1997;50(5):71.*
Yoon et al., Cancer Research, vol. 60, pp. 1117-1120 (Feb. 15, 2000).
Yu et al., Electrophoresis, vol. 21, pp. 3058-3068 (2000).
Bini et al., Electrophoresis, vol. 18, pp. 2832-2841 (1997).
Celis et al., Electrophoresis, vol. 20, pp. 300-309 (1999).
Celis et al., "Short-term culturing of low-grade superficial bladder transitional cell carcinomas leads to changes in the expression levels of several proteins involved in key cellular activities" *Electrophoresis*, 20, pp. 355-361 (1999).
Syrigos et al., "Use of Monoclonal Antibodies for the Diagnosis and Treatment of Bladder Cancer" *Hybridoma*, vol. 18, No. 3 (1999).
Konety et al., "Urine Based Markers of Urological Malignancy" *The Journal of Urology*, vol. 165, pp. 600-611 (2001).
Kageyama et al., "Identification by Proteomic Analysis of Calreticulin as a Marker for Bladder Cancer and Evaluation of the Diagnostic Accuracy of Its Detection in Urine" *Clinical Chemistry*,50:5, pp. 857-866 (2004).

* cited by examiner

*Primary Examiner*—Shanon Foley
*Assistant Examiner*—Lei Yoa
(74) *Attorney, Agent, or Firm*—Birch, Stewart, Kolasch & Birch, LLP

(57) ABSTRACT

This invention relates to a method for detecting urothelial carcinoma using an antibody that specifically reacts with a calreticulin protein or a fragment thereof and immunoassaying a calreticulin protein in a sample.

5 Claims, 1 Drawing Sheet

Fig. 1

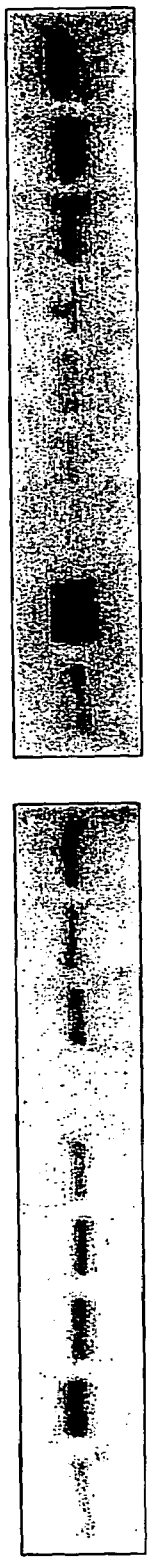

Western blot for U2 in urine (urine 37.5 μL derived from ECL plus)

Bladder carcinoma, G2, class I, <1cm

Renal pelvic carcinoma, SCC, class V, 1~3cm

Bladder carcinoma CIS, G3, class V

Renal pelvic carcinoma, G3, class I, <1cm

Bladder carcinoma, G1, class I, <1cm

Bladder carcinoma, G3, class V, 1~3cm

Bladder carcinoma, G3, class IV, 1~3cm

Renal pelvic carcinoma, G2, class I, 1~3cm

Bladder carcinoma, G3, class III, 1~3cm

Bladder carcinoma CIS, G3, class V

Bladder carcinoma, G2, class IV, <1cm

Bladder carcinoma, G2, class I, 1~3cm

Bladder carcinoma, G1, class I, <1cm

Bladder carcinoma, G2, class I, <1cm

Bladder carcinoma, G3, class V, 1~3cm

Bladder carcinoma, G2, class I, 1~3cm

Bladder carcinoma, G3, class V, <1cm

Bladder carcinoma, G3, class V, <1cm

TUMOR MARKER FOR UROTHELIAL CARCINOMA

TECHNICAL FIELD

The present invention relates to a protein useful for diagnosing urothelial carcinoma and a method for detecting urothelial carcinoma through the assay of the protein.

BACKGROUND ART

In the category of urogenital carcinomas, the number of persons who are affected with urothelial carcinoma (such as bladder carcinoma or renal pelvic and ureteral carcinoma) is the second only to those suffering from prostate carcinoma. In Japan, in a single year, 7,886 males and 2,697 females are affected with bladder carcinoma (1994, Foundation for Promotion of Cancer Research). The number of persons dying therefrom is 2,856 males and 1,277 females (1997, same as above). This carcinoma is the fifth most common among all types of carcinomas in the United States. Since approximately 70% of these patients experience repeat carcinoma recurrence in their urinary tracts, the number of patients is deduced to be constantly as large as several tens of thousands in Japan alone, including examples of follow-up cases. In physical examinations, erythrocyturia presenting 5 or more blood erythrocytes per visual field is observed in about 3% of general males and about 7% of general females. Accordingly, the number of persons to be subjected to screening for urothelial carcinoma is enormous. In general, cystoscopy is a decisive factor for the confirmed diagnosis. However, it is unsuitable for mass screening since this process is invasive and expensive. Thus, there was an urgent need to develop a diagnostic technique that is noninvasive, capable of dealing with a large number of specimens, and excellent in sensitivity and specificity. Urine cytology is a representative noninvasive examination, which has the longest history of clinical application. While this technique is excellent in specificity (95% to 100%), its sensitivity is low (40% to 60%). Sensitivity thereof is particularly deficient when examining well-differentiated carcinoma (0% to 15%). The sensitivity of auxiliary diagnosis using a bladder tumor antigen (BTA), Nuclear Matrix Protein 22 (NMP22), or the like, which has been recently put to practical use, is reported to be somewhat improved compared with that of cytodiagnosis of urine. The auxiliary diagnosis, however, are likely to indicate false-positive for gross hematuria or cystitis. Because of this low specificity, it has not yet resulted in a status exceeding that of urine cytology.

In the field of cancer research, however, expression of a protein referred to as a calreticulin protein is found to be enhanced in, for example, hepatocellular carcinoma (see Yoon G S. et al., Cancer Res, 60: 1117-1120, 2000 and Yu L R, et al., Electrophoresis, 21: 3058-3068, 2000) or breast carcinoma (see Bini L. et al., Electrophoresis, 18: 2832-2841, 1997). A calreticulin protein is only reported as a spot exhibiting enhanced expression appeared in the proteome analysis with respect to urothelial carcinoma (see Celis A. et al., electrophoresis, 20: 300-309, 1999). It has not yet been examined as a tumor marker for urothelial carcinoma.

DISCLOSURE OF THE INVENTION

Objects of the present invention are to discover a novel tumor marker for urothelial carcinoma and to provide a method for effectively detecting urothelial carcinoma.

The present inventors have conducted concentrated studies in order to attain the above objects. As a result, they have found that they could attain their objects by identifying a calreticulin protein as a tumor marker and using an antibody that specifically reacts with the marker. This has led to the completion of the present invention.

More specifically, the present invention includes the following inventions.

(1) A method for detecting urothelial carcinoma by assaying a calreticulin protein in a sample.

(2) A method for detecting urothelial carcinoma comprising immunologically determining a calreticulin protein in a sample by using an antibody that specifically reacts with a calreticulin protein or a fragment thereof.

(3) The method according to (1) or (2), wherein the sample is urine.

(4) A diagnostic agent for urothelial carcinoma comprising an antibody that specifically reacts with a calreticulin protein or a fragment thereof.

(5) A kit for diagnosing urothelial carcinoma comprising an antibody that specifically reacts with a calreticulin protein or a fragment thereof.

The proteomics process (proteome analysis) that directly analyzes expressed proteins was selected as a method for screening candidate substances, instead of differential display that targets mRNA (cDNA). Specifically, proteins changed in cancer that are more specifically or significantly expressed in carcinoma tissues than in normal tissues were searched for and identified. Thereafter, the expression levels of these proteins in body fluids were examined. Reasons therefor are as follows. (i) The assay object of the currently stable quantitative detection system is not a gene but a protein. (ii) The coefficient of correlation between the mRNA (cDNA) level and the protein level is not necessarily high, i.e., the difference in the gene expression level cannot be always confirmed in protein expression level. (iii) The existence of a protein for the discovered mRNA cannot always be verified. (iv) Expressions of some genes are regulated at the translation level rather than the transcription level. (v) Theoretically, changes in the expression level resulting from post-translational protein modification or the surrounding environment cannot be understood from experimentation based on the gene. There may be other factors. More specifically, the final target is a protein, and thus, it should be focused, from the beginning, on the proteins existing in an amount more than the detection limit of the current analytical system.

Based on the above principle, the present inventors had screened for proteins, the expressions of which were enhanced in urothelial carcinoma cells in comparison with normal urothelial cells, on the basis of proteome analysis. As a result, it was found that there was a significant difference in the expression level of full-length calreticulin proteins between normal urothelial tissues and urothelial carcinoma tissues. Further, the present inventors have immunoligically assayed the level of calreticulin protein in the urine of patients with non-urothelial carcinoma and patients with urothelial carcinoma. As a result, they have found that the calreticulin protein was detected with high specificity and sensitivity in the urine of patients with urothelial carcinoma. The term "patients with non-urothelial carcinoma" refers to patients who are not affected with urothelial carcinoma, but affected with urolithiasis, prostate carcinoma, prostatic hyperplasia, renal cell carcinoma, or hypospadias. More specifically, the present invention relates to a method for detecting urothelial carcinoma, comprising immunologically quantifying the calreticulin protein in a sample by using an antibody that specifically reacts with the calreticulin protein or a fragment thereof. The method for detecting urothelial carcinoma according to the present invention enables dinstinguishment between patients with urothelial carcinoma and patients with non-urothelial carcinoma as described above.

A Calreticulin Protein

A calreticulin (CRT) protein is a 46 kDa protein comprising 400 amino acid residues localized in the endoplasmic reticulum. This protein is not only distributed in many tissues but also is conserved in a wide variety of species ranging from higher plants to mammalians. It was initially discovered as a calcium-binding protein, although its function as molecular chaperon has recently drawn attention. Moreover, this protein is very important for organisms that have a wide variety of functions such as cell adhesion or the activation of gene expression by binding of steroid hormones and stress response.

THE ANTIBODY OF THE PRESENT INVENTION

An antibody that can be used in the present invention is not particularly limited as long as it specifically reacts with a calreticulin protein or a fragment thereof. A monoclonal or polyclonal antibody can be used, and the use of a monoclonal antibody is preferable. An antibody that reacts with the C-terminus of the calreticulin protein is particularly preferable. The globulin type of the antibody of the present invention is not particularly limited as long as it has the aforementioned feature. It may be IgG, IgM, IgA, IgE, or IgD, and IgG and IgM are preferable. For example, SPA-600 (StressGen) can be used as a polyclonal antibody, and SPA-601 (StressGen) can be used as a monoclonal antibody. An antibody that specifically reacts with the calreticulin protein can be prepared by a method described below.

(1) Preparation of an Immunogen

In order to prepare the monoclonal antibody of the present invention, a protein as an immunogen (antigen) is prepared. A calreticulin protein or a fragment thereof is used as an immunogen protein. The amino acid sequence of a calreticulin protein that can be used as an immunogen in the present invention and the cDNA sequence that encodes this protein are disclosed under the accession number AD000092 in GenBank. Accordingly, a calreticulin protein fragment to be used as an immunogen can be synthesized utilizing the disclosed amino acid sequence information by a technique known in the art, such as solid phase peptide synthesis. When a calreticulin protein fragment is used as an immunogen, it is preferably ligated to a carrier protein such as KLH or BSA.

Alternatively, a calreticulin protein can be produced using the information of cDNA encoding the calreticulin protein by a known gene recombination technique. Production of the calreticulin protein using the gene recombination technique is hereafter described.

A recombinant vector for producing calreticulin can be obtained by ligating the disclosed cDNA sequence to an adequate vector. A transformant can be obtained by introducing the recombinant vector for producing calreticulin to a host so that the calreticulin protein can be expressed.

Phage DNA or plasmid DNA that can be autonomously multiplied in a host microorganism can be used as a vector. Plasmid DNA includes: plasmids derived from *E. coli* such as pET21a, pGEX4T, pUC118, pUC119, pUC18, or pUC19; plasmids derived from *Bacillus subtilis* such as pUB110 or pTP5; and plasmids derived from yeast such as YEp13, YEp24, or YCp50. Phage DNA includes λ phages such as λgt11 or λZAP. Further, an animal virus such as vaccinia virus or an insect virus vector such as baculovirus can also be used as a vector.

In order to insert the calreticulin cDNA into a vector, for example, a method may be employed in which the purified DNA is first cleaved with an appropriate restriction enzyme and then inserted into the restriction site or the multi-cloning site of an appropriate vector DNA thereby ligated to the vector.

In addition to a promoter and the calreticulin cDNA, cis elements such as an enhancer, a splicing signal, a poly(A) addition signal, a selection marker, a ribosome binding sequence (SD sequence), or the like may optionally be ligated to the recombinant vector for producing calreticulin in mammalian cells.

A known DNA ligase is used to ligate a DNA fragment to a vector fragment. The DNA fragment and the vector fragment are annealed and then ligated to each other. Thus, a recombinant vector for producing calreticulin is prepared.

A host that is used for transformation is not particularly limited as long as the calreticulin protein can be expressed therein. Examples thereof include bacteria such as *E. coli* or *Bacillus subtilis*, yeast, animal cells such as COS cells or CHO cells, and insect cells.

For example, when a bacterium is used as the host, the recombinant vector for producing calreticulin is autonomously replicable inside the host and, at the same time, it preferably comprises a promoter, a ribosome binding sequence, the calreticulin DNA, and a transcription termination sequence. It may contain a promoter-regulating gene. An example of *E. coli* includes *Escherichia coli* BRL, and an example of hay *bacillus* includes *Bacillus subtilis*. Any promoter may be used as long as it can be expressed in a host such as *E. coli*. A method for introducing a recombinant vector in a bacterium is not particularly limited as long as DNA can be introduced to a bacterium via such method. Examples thereof include a method using calcium ions and electroporation.

When yeast, animal cells, insect cells, or the like are used as hosts, the calreticulin protein can be produced in the same manner in accordance with a technique known in the art. The calreticulin protein used as an immunogen in the present invention can be obtained by culturing the transformant obtained above and recovering the protein from the resultant culture product. The term "culture product" means any of the following materials, i.e., culture supernatant, cultured cells, cultured microorganisms, or disrupted cells or microorganisms. The aforementioned transformant is cultured in a medium by conventional methods for culturing a host.

As a medium for culturing the transformant obtained from a host microorganism such as *E. coli* or yeast, either a natural or synthetic medium may be used as long as it contains carbon sources assimilable by the microorganism, nitrogen sources, and inorganic salts and is capable of efficient culture of the transformant.

Usually, the culture is carried out under aerobic conditions (such as shaking culture or aeration agitation culture) at 37° C. for 6 to 24 hours. During the culture, the pH is maintained at an approximately neutral level. The pH is adjusted with an inorganic or organic acid, an alkali solution, or the like. During the culture, an antibiotic such as ampicillin or tetracycline may be added to the medium, if necessary.

After the culture, the protein is extracted by disrupting the cultured microorganism or cell if the calreticulin protein is produced in the microorganism or cell. If the calreticulin protein is secreted outside of the microorganism or cell, the culture fluid may be used as it is or subjected to centrifugation or the like to remove the microorganism or cells. Thereafter, conventional biochemical techniques used for isolating/purifying a protein, for example, ammonium sulfate precipitation, gel chromatography, ion exchange chromatography, and affinity chromatography, can be employed independently or in an appropriate combination to isolate and purify the calreticulin protein from the above culture product.

Whether or not the calreticulin protein was obtained can be confirmed by SDS-polyacrylamide gel electrophoresis or other means.

Subsequently, the obtained protein is dissolved in a buffer to prepare an immunogen. If necessary, an adjuvant may be added for effective immunization. Examples of an adjuvant include commercially available Freund's complete and incomplete adjuvants. Any of these may be mixed.

(2) Preparation of a Monoclonal Antibody (i) Immunization and Recovery of Antibody-Producing Cells The thus obtained immunogen is administered to a mammalian such as a rat, mouse (e.g., the inbred line mouse, BALB/c), or rabbit. The amount of an immunogen per dose is adequately determined in accordance with the type of animal to be immunized or the route of administration. It is about 50 µg to 200 µg per animal. Immunization is mainly performed by intravenously, subcutaneously, or intraperitoneally injecting an immunogen. The intervals of immunization are not particularly limited. After the initial immunization, additional immunization is performed two to six times, and preferably 3 or 4 times at intervals of several days to several weeks, and preferably at intervals of 1 to 4 weeks. After the initial immunization, the antibody titer of serum from the immunized animal is repeatedly assayed by enzyme-linked immuno sorbent assay (ELISA) or other means. When the antibody titer has reached the plateau region, the immunogen is intravenously or intraperitoneally injected as the final immunization. Two to five days after the final immunization, preferably three days later, antibody-producing cells are recovered. Antibody-producing cells include spleen cells, lymph node cells, and peripheral blood cells, and spleen cells or local lymph node cells are preferable.

(ii) Cell Fusion

The antibody-producing cells obtained from the immunized animal as mentioned above and myeloma cells are subjected to cell fusion to obtain hybridomas.

Established cell lines of animals such as mice that are generally available can be used as myeloma cells to be fused with antibody-producing cells. A preferable cell line has drug selectivity, and it cannot survive in a HAT-selective medium (containing hypoxanthine, aminopterin, and thymidine) in an unfused state while it can only survive in a fused state with an antibody-producing cell. An established cell line is preferably derived from an animal of the same species as the animal immunized. Specific examples of myeloma cells include hypoxanthine-guanine phosphoribosyltransferase (HGPRT) deficient cell lines derived from BALB/c mice such as P3X63-Ag.8 (ATCC TIB9), P3X63-Ag.8.U1 (Japanese Collection of Research Bioresources (JCRB) 9085), P3/NSI/1-Ag4-1 (JCRB 0009), P3x63Ag8.653 (JCRB 0028), and Sp2/0-Ag14 (JCRB 0029).

Subsequently, the myeloma cells are subjected to cell fusion with antibody-producing cells. Cell fusion is carried out by mixing antibody-producing cells with myeloma cells at ratios of about 1:1 to 20:1 in a medium for culturing animal cells such as serum-free DMEM or RPMI-1640 medium and in the presence of a cell fusion accelerator. Polyethylene glycol or the like having an average molecular weight of 1,500 to 4,000 Daltons can be used as a cell fusion accelerator at a concentration of about 10% to 80%. If necessary, an adjuvant such as dimethyl sulfoxide may be used together to enhance the fusion efficiency. Further, antibody-producing cells can be fused with myeloma cells using a commercially available apparatus for cell fusion that utilizes electric stimulus such as electroporation.

(iii) Selection and Cloning of Hybridomas

Hybridomas of interest are selected from cells after cell fusion. A cell suspension is adequately diluted with, for example, fetal bovine serum-containing RPMI-1640 medium, and the resultant is sowed on a microtiter plate in amounts of approximately $2 \times 10^5$ cells/well. A selection medium is added to each well, and a selection medium is thereafter adequately exchanged to perform culture. Culture temperature is 20° C. to 40° C., and preferably about 37° C. When myeloma cells are HGPRT deficient or thymidine kinase (TK) deficient, a selection medium containing hypoxanthine, aminopterin, and thymidine (HAT medium) can be used to selectively culture and multiply only hybridomas of antibody-producing cells and myeloma cells. As a result, cells that begin to grow approximately 14 days after the initiation of culture in the selection medium can be obtained as hybridomas.

Screening is then carried out to inspect whether or not antibodies of interest are present in the culture supernatant of multiplied hybridomas. Hybridomas may be screened in accordance with a conventional technique without particular limitation. For example, a portion of the culture supernatant contained in the well that was grown as hybridomas is recovered and then assayed by a technique of enzyme immunoassay (enzyme immuno assay (EIA) or ELISA) or radioimmunoassay (RIA).

Fused cells are cloned by limiting dilution or other means to finally establish hybridomas that are monoclonal antibody-producing cells. The hybridomas of the present invention are stable while being cultured in a basal medium such as RPMI-1640 or DMEM as described below. They produce and secrete monoclonal antibodies that specifically react with calreticulin proteins derived from urothelial carcinoma.

(iv) Recovery of Monoclonal Antibodies

Monoclonal antibodies can be recovered from the established hybridomas by, for example, a conventional technique for cell culture or ascites-producing technique.

In a cell culture technique, hybridomas are cultured in a medium for culturing animal cells such as 10% fetal bovine serum-containing RPMI-1640 medium, MEM medium, or serum-free medium under conventional culture conditions (for example, at 37° C. in the presence of 5% $CO_2$) for 2 to 10 days. Antibodies are obtained from the culture supernatant thereof.

In the case of the ascites-producing technique, hybridomas are administered intraperitoneally to the animals of species that are same as the origin of myeloma cells in amounts of about $1 \times 10^7$ cells to mass-multiply hybridomas. Ascites or serum are recovered 1 to 2 weeks thereafter.

When the aforementioned technique for recovering antibodies requires the purification of the antibodies, a known technique such as ammonium sulfate precipitation, ion exchange chromatography, affinity chromatography, or gel chromatography is adequately selected. Alternatively, these techniques are adequately combined. Thus, the purified monoclonal antibodies of the present invention can be obtained.

(3) Preparation of Polyclonal Antibodies

Polyclonal antibodies are prepared as follows. Animals are immunized in the same manner as described above, the antibody titers are assayed by, for example, enzyme immunoassay (EIA and ELISA) or radioimmunoassay (RIA) 6 to 60 days after the final immunization, and blood is sampled when the maximal antibody titer was indicated, thereby obtaining antiserum. Thereafter, reactivity of the polyclonal antibodies in antiserum is assayed by ELISA or other techniques.

A Method for Detecting Urothelial Carcinoma

In the method for detecting urothelial carcinoma according to the present invention, the aforementioned antibodies are used to immunologically assay the calreticulin protein derived from urothelial carcinoma cells in a sample. In this specification, "detection" includes both of the inspection of the presence or absence of the calreticulin protein in a sample and the measurement of the amount thereof.

The term "urothelial carcinoma" used in this specification refers to carcinoma that is generated in transitional epithelium located in the renal calyx, renal pelvis, ureter, bladder, or urethra. Examples of urothelial carcinoma include bladder carcinoma, renal pelvic carcinoma, ureteral carcinoma, and urethral carcinoma. The present invention is particularly preferably used for detecting bladder carcinoma.

The detection method according to the present invention can employ any method using an antibody, which is an immunoassay, as long as the method uses the aforementioned antibody of the present invention. For example, the detection method of the present invention is carried out by means of, for example, enzyme immunoassay (ELISA or EIA), fluoroimmunoassay, radioimmunoassay (RIA), luminescence immunoassay, immunoturbidimetry, immunonephelometry, latex aggregation, latex turbidimetry, blood erythrocyte aggregation, particle aggregation, or Western blotting.

A sample to be analyzed in the detection method of the present invention is not particularly limited as long as it is a biological sample that may contain a calreticulin protein derived from urothelial carcinoma. Examples thereof include blood, serum, plasma, culture supernatant of lymphocytes, urine, spinal fluid, saliva, sweat, and ascites. Extracts of cells, organs, or the like can also be used. The assay values of calreticulin proteins obtained in a sample such as urine or serum are particularly useful as indicators for urothelial carcinoma. Thus, the method for detecting urothelial carcinoma according to the present invention is effective not only in carcinoma tissues but also in urine, and therefore, it is very useful as a simple detection method.

When the detection method of the present invention is carried out by means of immunoassay that utilizes labeling, such as enzyme immunoassay, fluoroimmunoassay, radioimmunoassay, or luminescence immunoassay, the antibody of the present invention or an ingredient in the sample is preferably immobilized to solid-phase and then immunological reaction is effected.

Solid-phase supports that can be used include insoluble supports in the forms of, for example, beads, microplates, test tubes, sticks, and test strips composed of materials such as polystyrene, polycarbonate, polyvinyltoluene, polypropyrene, polyethylene, polyvinyl chloride, nylon, polymethacrylate, latex, gelatin, agarose, cellulose, sepharose, glass, metal, ceramic, or magnet. A solid-phase support can be bound to the antibody of the present invention or an ingredient of a sample in accordance with a conventional technique such as physical adsorption or chemical binding. Alternatively, these techniques may be used in combination. Thus, immobilization to solid-phase can be provided.

In the present invention, the reaction is directly detected by labeling the antibody of the present invention in order to easily detect a reaction between the antibody of the present invention and the calreticulin protein derived from urothelial carcinoma cells in a sample. Alternatively, the reaction may be indirectly detected with the use of a labeled secondary antibody. In the detection method according to the present invention, the latter form of indirect detection (such as via the sandwich method) is preferably employed from the point of sensitivity.

In the case of enzyme immunoassay, peroxidase (POD), alkaline phosphatase, β-galactosidase, urease, catalase, glucose oxidase, lactate dehydrogenase, amylase, a biotin-avidin complex, or the like can be used as a labeling substance. In the case of fluoroimmunoassay, fluorescein isothiocyanate, tetramethylrhodamine isothiocyanate, substituted rhodamine isothiocyanate, dichlorotriazine isothiocyanate, Alexa-480, or AlexaFluor-488 can be used as a labeling substance. In the case of radioimmunoassay, tritium, iodine-125, or iodine-131 can be used as a labeling substance. In luminescence immunoassay, for example, an NADH-FMNH$_2$-luciferase, luminol-hydrogen peroxide-POD, acridinium ester, or dioxetane compound can be used.

In the case of enzyme immunoassay, a labeling substance can be bound to an antibody by a conventional technique such as the glutaraldehyde method, the maleimide method, the pyridyl disulfide method, or the periodic acid method. In the case of radioimmunoassay, a conventional technique such as the chloramine-T method or the Bolton-Hunter method can be employed.

Assay can be carried out in accordance with known techniques described in: "Rinshou byouri (Clinical Pathology), Rinshou kensa no tameno imunoassei (Immunoassay for clinical assay—Techniques and applications—)," Extra Special Features, No. 53, the Japan Society of Clinical Pathology (ed.), the Clinical Pathology Press, 1983; "Kouso men-eki sokuteihou (Enzyme Immunoassay)," Eiji Ishikawa et al. (ed.), vol. 3, Igaku-Shoin Ltd., 1987; "Tanpakushitsu, Kakusan, Kouso (Protein, Nucleic Acid, Enzyme), Supplementary volume 31, Kouso men-eki sokuteihou (Enzyme Immunoassay)," Tsunehiro Kitagawa et al. (ed.), Kyoritsu Shuppan Co., Ltd., 1987; "Rajio imunoassei (Radioimmunoassay)","Minoru Irie (ed.), Kodansha Scientific Ltd., 1974; or "Zoku Rajio Imunoassei (Radioimmunoassay (sequal))," Minoru Irie (ed.), Kodansha Scientific Ltd., 1979.

For example, when the antibody of the present invention is directly labeled, ingredients in a sample are immobilized to solid-phase, and the resultant is brought into contact with the labeled antibody of the present invention, thereby forming a complex of a calreticulin protein and the antibody of the present invention. Unbound labeled antibodies are washed and separated, thereby assaying the level of calreticulin proteins in the sample based on the amount of bound labeled antibodies or that of unbound labeled antibodies.

Alternatively, when a labeled secondary antibody is used, for example, the antibody of the present invention is allowed to react with a sample (the primary reaction), and the labeled secondary antibody is further allowed to react with the resultant (the secondary reaction). The primary reaction and the secondary reaction may be carried out in the opposite order, simultaneously, or with some time intervals therebetween. Through the primary and the secondary reactions, a immobilized complex of the calreticulin protein—the antibody of the present invention—the labeled secondary antibody or a immobilized complex of the antibody of the present invention—the calreticulin protein—the labeled secondary antibody can be prepared. Unbound labeled secondary antibodies are then washed and separated, thereby assaying the level of calreticulin proteins in the sample based on the amount of bound labeled secondary antibodies or that of unbound labeled secondary antibodies.

More specifically, in the case of enzyme immunoassay, a marker enzyme is reacted with a substrate under its optimal conditions, and the amount of the reaction product is assayed by an optical or other technique. In the case of fluoroimmunoassay, the fluorescence intensity derived from fluorescent labeling is assayed. In the case of radioimmunoassay, the level of radioactivity derived from radiolabeling is assayed. In the case of luminescence immunoassay, the level of luminescence derived from the luminescent reaction system is assayed.

In the detection method of the present invention, the generation of immune complex aggregates resulted in, for example, immunoturbidimetry, latex aggregation, latex turbidimetry, blood erythrocyte aggregation, or particle aggregation can be optically assayed based on a transmitted beam or scattered beam, or visually assayed using a phosphate buffer, a glycine buffer, a Tris buffer, or a Good's buffer as a solvent. Further, a reaction accelerator such as polyethylene glycol or an inhibitor against non-specific reaction may be contained.

A preferable embodiment of the detection method of the present invention is hereafter described. At first, the antibody of the present invention is immobilized on an insoluble support as a primary antibody. Preferably, the surface of a solid-phase support that has no antigen adsorbed thereon is blocked with a protein (e.g., calf serum, bovine serum albumin, or gelatin) unrelated to the antigen. Subsequently, the immobilized primary antibody is brought into contact with a test sample. The resultant is then brought into contact with a labeled secondary antibody that reacts with a calreticulin protein at a site different from that for the primary antibody, and signals from the label are detected.

The "secondary antibody that reacts with a calreticulin protein at a site different from that for the primary antibody" used herein is not particularly limited as long as it recognizes a site other than the binding site for the primary antibody with the calreticulin protein. Also, a type of immunogen thereof is not limited. Any of the polyclonal antibody, antiserum, or the monoclonal antibody may be used, and fragments of these antibodies (e.g., Fab, F(ab')$_2$, or Fab') can also be used. Further, several types of monoclonal antibodies may be used as secondary antibodies.

In contrast, the antibody of the present invention may be labeled to prepare a secondary antibody, an antibody that reacts with the calreticulin protein at a site different from that for the antibody of the present invention may be immobilized on an insoluble support as a primary antibody, the immobilized primary antibody may be brought into contact with a test sample, and the resultant may be then brought into contact with the antibody of the present invention that is labeled as a secondary antibody, thereby detecting signals from the label.

A Diagnostic Agent for Urothelial Carcinoma

As described above, the antibody of the present invention can be used as a diagnostic agent for carcinoma since it specifically reacts with the calreticulin protein derived from urothelial carcinoma cells.

The diagnostic agent of the present invention comprises the antibody of the present invention. Accordingly, whether or not an individual is affected with urothelial carcinoma can be diagnosed with the use of the diagnostic agent of the present invention by detecting the calreticulin protein derived from urothelial carcinoma cells contained in the sample collected from the individual who is suspected to be affected with urothelial carcinoma.

The diagnostic agent of the present invention can be used in any immunoassay technique. The use thereof in combination with a simple technique known in the art such as a test strip for immunochromatography enables a simpler and more rapid diagnosis of carcinoma. The test strip for immunochromatography is constituted by, for example, a sample receptor made of a material that easily absorbs a sample, a reagent portion comprising the diagnostic agent of the present invention, a development portion for a reaction product of the sample and the diagnostic agent to move, a labeling portion for coloring the developed reaction product, and a presenting portion to which the colored reaction product is developed. This can be prepared in a form similar to that of a pregnancy test. At the outset, a sample is applied to the sample receptor and the sample receptor absorbs the sample to bring it to the reagent portion. In the reagent portion, reaction is then initiated between the calreticulin protein derived from urothelial carcinoma cells in the sample and the antibody of the present invention, and the reacted complex moves through the development portion and reaches the labeling portion. In the labeling portion, reaction is initiated between the reaction complex and the labeled secondary antibody, and the reaction product with the labeled secondary antibody is expanded to the presenting portion. Thus, coloring can be observed.

The test strip for immunochromatography does not impart any pain or risk resulting from the use of the reagent to users. Thus, it can be used for monitoring at home. The results can be thoroughly examined, and treatment can take place (e.g., via surgical removal) at an adequate medical institution. This can lead to the prevention of metastasis or recurrence. At present, this kind of test strip can be inexpensively mass-produced by the production method described in, for example, JP Patent Publication (Kokai) No. 10-54830 A (1998).

Also, use of the diagnostic agent of the present invention in combination with a known diagnosing agent for a tumor marker of urothelial carcinoma enables more reliable diagnosis.

A Kit for Diagnosing Urothelial Carcinoma

The present invention also relates to a kit for diagnosing urothelial carcinoma comprising an antibody that specifically reacts with a calreticulin protein or a fragment thereof. In the kit of the present invention, the antibody may be bound to the aforementioned solid-phase support. Further, the kit of the present invention can comprise a labeled secondary antibody, a support, a washing buffer, a sample diluent, an enzyme substrate, a reaction terminator, a calreticulin protein as a purified standard substance, or the like.

BRIEF DESCRIPTION OF THE DRAWING

FIG. 1 shows the results of immunoblotting using the SPA-600 antibody in which urine derived from patients having urothelial carcinomas with various levels of differentiation and various tumor diameters are subjected to one-dimensional electrophoresis, the resultant is then transferred to the PVDF membrane. G1 to G3 indicate the levels of differentiation (i.e., degree of malignancy) of tumors that are histologically classified as transitional cell carcinomas among urothelial carcinomas, SCC indicates squamous cell carcinoma, classes I to V indicate results of cytodiagnosis of urine, and numerical values indicate tumor diameters.

This description includes part or all of the contents as disclosed in the description and/or drawing of Japanese Patent Application No. 2002-320355, which is a priority document of the present application.

BEST MODES FOR CARRYING OUT THE INVENTION

The present invention is hereafter described in more detail with reference to the following examples, although the technical scope of the present invention is not limited thereto.

EXAMPLE 1

Screening of Proteins Changed in Cancer by the Proteome Analysis (1) Preparation of Samples Three specimens of bladder transitional cell carcinoma obtained through surgical operations (surgical operations: two examples of transurethral resection of bladder tumor and one example of total cystectomy; grade of atypism: one example of grade 2 and two examples of grade 3) were used as samples. Normal mucous membranes of urinary bladders obtained through retropubic prostatectomy for prostatic hyperplasia (two examples) and a normal ureter obtained through nephrectomy for renal cell carcinoma (one example) were used as controls. A tissue lysate comprising 8M urea, 2% CHAPS, 1% dithiothreitol (DTT), 0.5% Pharmalyte 3-10 (Amersham bioscience), 10% glycerol, and 1% protease inhibitor cocktail (Nacalai Tesque Inc.) was added, the mixture was homogenized, and the supernatant obtained by centrifugation at 15,000 rpm for 10 minutes was determined to be a solution of solubilized tissues. In order to perform the subsequent isoelectric focusing with high voltage, desalting was carried out using the MicroSpin G-25 Column (Amersham Bioscience). Proteins were quantified by the Bradford assay using bovine serum albumin (Pierce) as a standard substance.

(2) First Dimension Isoelectric Focusing

Isoelectric focusing was carried out using the IPGphor (Amersham Bioscience). Immobilized pH gradient gel strips of various pH ranges were used (18 cm; pH levels: 4 to 7, 6 to 9, 4 to 5, 4.5 to 5.5, 5 to 6, and 5.5 to 6.7). For the gel image analysis, 80 μg (pH 4 to 7) and 120 μg (pH levels: 4 to 5, 4.5 to 5.5, 5 to 6, 5.5 to 6.7, and 6 to 9) of proteins were loaded per gel strip in accordance with the pH range, and the proteins were subjected to electrophoresis at a voltage of 8,000 V until they reached 32,000 Vh and 60,000 Vh, respectively. For protein identification, the amount of protein was 1 mg/gel regardless of the pH range.

(3) SDS-Treatment of Immobilized pH Gradient Gel Strip

The gel strip after the isoelectric focusing was equilibrated for 30 minutes in a buffer comprising 50 mM Tris-HCl (pH 6.8), 8M urea, 30% glycerol, 2% SDS, and 2% DTT.

(4) Second-Dimension SDS-Polyacrylamide Gel Electrophoresis

The second-dimension electrophoresis was carried out using 12.5% homogenous polyacrylamide gel (22×20×0.1 cm) at 20 mA/gel. An electrophoresis buffer comprising 25 mM Tris-base, 192 mM glycine, and 0.1% SDS was used.

(5) Silver Staining (Nonglutaraldehyde-Fixed)

Gel was fixed with 30% ethanol and 10% acetic acid, washed with 20% ethanol and ultrapure water, and then sensitized with 0.02% sodium thiosulfate. The resultant was reacted with a solution of 0.2% silver nitrate, rinsed with ultrapure water, and then developed with 0.025% formalin, 0.001% sodium thiosulfate, and 3% potassium carbonate. Color development was terminated with the use of 2.5% acetic acid and 0.4M Tris-base.

(6) Incorporation of Gel Image and Spot Detection

A gel image was incorporated using a reflective flatbed scanner. Spot was detected using an automatic detection function (silver stain mode) of the PDQUEST Ver. 5.1 (pdi), which is software for analyzing two-dimensional electrophoresis gel. Further, spots remaining unrecognized were visually inspected and then added.

(7) Comparison of Gel Images Between Normal Tissues and Carcinoma Tissues

Spots were visually compared between three carcinoma examples and three controls. When these groups were compared, only spots that exhibited development and enhancement or disappearance and attenuation common to all examples in each group were selected as those with varied expressions.

(8) In-Gel Digestion, Desalting and Concentration

The method of Gharahdaghi et al. (Electrophoresis, 1999) was modified and then carried out. The cleaved gel was desilverized with 15 mM potassium ferricyanide and 50 mM sodium thiosulfate. Cysteine residues were reduced to be alkylated using 10 mM DTT and 50 mM iodoacetamide, and the resultant was subjected to enzyme treatment with trypsin (Promega, sequencing grade) at 37° C. overnight. A solution of degraded peptide fragments was recovered and then subjected to desalting and concentration using the ZipTip C18 Column (Millipore). The resultant was then mixed with a matrix (a saturated solution of α-cyano-4-hydroxycinnamic acid), the mixture was applied dropwise on a sample plate of the mass spectrometer, and dried.

(9) Mass Spectrometry by MALDI/TOF-MS

The Voyager RP (PerSeptive Biosystems) for MALDI/TOF-MS was used as the mass spectrometer in the modes of reflectron and delayed ion extraction. des-Arg-Bradykinin (904.468 (Charge+1)) ACTH (18-39 clips) (2465.2) was used as an external standard for calibration, and two trypsin autolysates (842.510, 2211.1) were used as internal standards.

(10) Protein Identification Using a Mass Spectrometry Database

Proteins were identified by the peptide mass fingerprint (PMF) technique. Two types of peptide mass databases, MS-Fit and PeptideSearch, were used in combination. The peptide mass was monoisotopic, and the allowable limit of error was within ±100 ppm.

(Results)

In the two-dimensional electrophoresis gel having a narrow pH range, 15 groups of spots exhibiting significant expression in carcinoma tissues were distinguished, and the names of proteins corresponding to 9 spots containing calreticulin proteins were identified by PMF.

EXAMPLE 2

Examination of Usefulness as a Tumor Marker (1) Confirmation of a Calreticulin Protein Spot by Two-Dimensional Immunoblotting The gel subjected to two-dimensional electrophoresis was transferred to the Immobilon PVDF membrane (Millipore), and the membrane was subjected to immunoblotting using the monoclonal antibody SPA-601 (StressGen) against recombinant human calreticulin proteins and the polyclonal antibody SPA-600 (StressGen) having the synthetic peptide of the human calreticulin protein-C-terminus as an immunogen. Blocking was carried out using the Super Block Blocking Solution in TBS (Pierce) at 4° C. overnight. The dilution rate for the SPA-601 antibody was 10,000-fold, that for the SPA-600 antibody was 20,000-fold, that for the HRP labeled anti-mouse IgG antibody (MBL) was 10,000-fold, and that for the HRP labeled anti-rabbit IgG antibody (Vector) was 50,000-fold. 10 mM Tris-HCl (pH 7.4), 100 mM NaCl, and 0.1% Tween 20 were used for washing and dilution of antibody. Bands were detected using chemoluminescence by ECL (Amersham Bioscience) and then exposed to the X-ray film.

As a result of the two-dimensional immunoblotting (pH 4 to 7) using the antibody SPA-601, a weak spot (pI of approximately 4.5, 40 kDa) was detected in urothelial carcinoma tissues other than the spot (pI of approximately 4.3, 55 kDa) corresponding to the calreticulin protein. In contrast, the spot of the calreticulin protein was very weakly expressed while the spot of the 40 kDa was strongly expressed in normal urothelial tissues.

Proteins were transferred from the electrophoresed gel to a Sequiblot PVDF membrane (BioRad) using the Multiphor II NovaBlot Kit (Amersham Bioscience) in which a buffer comprising aminocaproic acid is used. The PVDF membrane was stained with CBBR 250. The spots of interest were cleaved out, and the N-terminal sequences were determined by Edman degradation. Through the analysis of the N-terminal amino acid sequence, the sequence EPAVYFKEQF was found in both spots. This was consistent with amino acids 1 to 10 in the primary structure of the human calreticulin protein.

In the two-dimensional immunoblotting using the SPA-600 antibody recognizing the C-terminus of the calreticulin protein, only the spot that was consistent with the calreticulin protein was recognized. Thus, a 40-kDa calreticulin protein was considered to be a molecular species that was cleaved at a site on the C-terminal side. Accordingly, the protein whose expression level was significantly varied between normal urothelial tissues and carcinoma tissues was considered to be a full-length calreticulin protein (pI: 4.3, 55 kDa). Thus, use of the C-terminus-recognizing SPA-600 antibody was used in the succeeding examinations.

(2) Immunoprecipitation Using the SPA-600 Antibody

Prior to the evaluation of many specimens, an immunoprecipitation experiment was performed using the SPA-600 antibody recognizing the C-terminus of the calretidulin protein. This was performed in order to inspect whether or not other molecular species that can be detected by the SPA-600 antibody, especially a carcinoma-specific molecular species, were observed in addition to the calreticulin protein. Urothelial carcinoma tissues were solubilized in a mixture of RIPA buffer (containing 50 mM Tris-HCl (pH 8.0), 150 mM NaCl, 1% Triton X-100, 0.5% deoxycholate, and 0.1% SDS) and a protease inhibitor. The Protein A Sepharose (Pharmacia) was used as a support for antibody binding. Normal rabbit serum was used as a control instead of an antibody. SDS-sample buffer (62.5 mM Tris-HCl (pH 6.8), 10% glycerol, 2% SDS, and 1% DTT) was added to eluate the precipitated complex of the support and the antibody resulted from immunoprecipitation, the supernatant after centrifugation was subjected to SDS-PAGE in 8% homogenous gel, and the gel was stained with silver. Also, immunoblotting was carried out using the SPA-601 antibody.

Among the precipitates obtained using the SPA-600 antibody, there was one calreticulin protein band that could be detected by immunoblotting using the SPA-601 antibody, and there was no finding that would suggest the existence of other molecular species.

(3) Immunoblotting of Calreticulin Protein in Normal Urothelial Tissues and in Urothelial Carcinoma Tissues In the same manner as described above, 22 specimens of urothelial carcinomas and 10 specimens of normal urothelial tissues were solubilized in a buffer, and protein was quantified. Proteins were diluted with the SDS-sample buffer to bring the amount of the protein in each lane to 1 µg. Proteins were separated by SDS-PAGE in 8% homogenous gel, and immunoblotting using the SPA-600 antibody was performed. The HeLa cell extract (1 µg, StressGen) was simultaneously electrophoresed in order to quantify the band.

The calreticulin protein band on the X-ray film was imaged using a light-transmitting flatbed scanner, followed by quantification using the Scion Image software (Scion Co.) for image analysis. The intensity of the band obtained from 1 µg of Hela cell extract was determined to be 1.0 unit.

The intensities of the calreticulin protein bands obtained from 1 pg of solution of solubilized tissue were 0.40±0.32 units (mean±SD) for normal urothelial tissues and 1.02±0.39 units (p=0.00014) for carcinoma tissues according to immunoblotting using the SPA-600 antibody. Based on the comparison between normal epithelial tissues and carcinoma tissues derived from the sample of the same example obtained by total cystectomy, a stronger calreticulin protein band was observed in carcinoma tissues.

EXAMPLE 3

Detection of Calreticulin Protein in Urine

In order to detect calreticulin proteins in urine, one-dimensional electrophoresis was carried out in the same manner as described above, the resultant was transferred to the PVDF membrane, and immunoblotting was then carried out using the SPA-600 antibody.

Twenty seven urine specimens of patients with urothelial carcinomas and 123 urine specimens of patients with non-urothelial carcinomas were used to compare the expression levels of calreticulin proteins in urine. These specimens were cryopreserved until the assay after they were collected.

As urine of patients with non-urothelial carcinomas, urine of patients who had, for example, prostatic hyperplasia, prostate carcinoma, urinary tract infection, renal cell carcinoma, urolithiasis, or idiopathic hematuria but did not have urothelial carcinoma were used.

As a result, weak calreticulin protein bands were detected by immunoblotting of only 22 examples (17.9%) among the 123 urine specimens of patients with non-urothelial carcinomas examined. In contrast, the calreticulin protein bands were detected in 19 examples (70.4%) among the 27 urine specimens of patients with urothelial carcinoma. The results are shown in Table 1 below.

TABLE 1

|  | Calreticulin | | |
| --- | --- | --- | --- |
| Urothelial carcinoma | Positive | Negative | Total |
| Affected | 19 | 8 | 27 |
| Not affected | 22 | 101 | 123 |
| Total | 41 | 109 | 150 |
| Sensitivity | | 19/27 | 70.4% |
| Specificity | | 101/123 | 82.1% |
| Ratio of positive reaction | | 19/41 | 46.3% |
| Rate of negative reaction | | 101/109 | 92.7% |

Further, patients who were diagnosed positive or negative for urothelial carcinoma in cytodiagnosis of urine were subjected to detection of calreticulin proteins in urine. The results obtained were compared. The results thereof are shown in Table 2 below.

TABLE 2

| Correlation with results of cytodiagnosis of urine in samples of urothelial carcinoma | | | |
| --- | --- | --- | --- |
|  | Calreticulin | | |
| Cytodiagnosis | Positive | Negative | Ratio of positive |
| Positive (IV, V) | 11 | 4 | 73.3% |
| Negative (I to III) | 8 | 4 | 66.7% |
| Total | 19 | 8 | |

The results shown in Table 2 indicate that the method of the present invention can detect carcinoma in examples of urothelial carcinoma that are diagnosed negative in cytodiagnosis of urine.

Urine of patients having urothelial carcinomas with various degrees of differentiation and various tumor diameters was similarly subjected to one-dimensional electrophoresis, transferrence to the PVDF membrane, and immunoblotting with the use of the SPA-600 antibody. The results of immunoblotting are shown in FIG. 1.

As is apparent from the results shown in FIG. 1, the method of the present invention enables the detection of calreticulin proteins even when the size of carcinoma is small or the degree of malignancy is low. Thus, urothelial carcinoma can be detected.

As is apparent from the above results, the calreticulin proteins can be detected with high sensitivity and specificity in urine of patients with urothelial carcinoma. Therefore, urothelial carcinoma can be effectively detected by assaying the calreticulin protein in patients' urine in accordance with the method of the present invention.

All publications, patents, and patent applications cited herein are incorporated herein by reference in their entirety.

INDUSTRIAL APPLICABILITY

The present invention enables the effective detection of urothelial carcinoma in a simple and cost-effective manner. Thus, early identification, diagnosis, and treatment of urothelial carcinoma can be implemented. Also, the method of the present invention can noninvasively detect urothelial carcinoma with the use of patient's urine. Thus, urothelial carcinoma can be simply and rapidly detected.

What is claimed is:

1. A method for detecting urothelial carcinoma which comprises the step of assaying bladder tissue or a urine sample from an individual suspected of being affected with urothelial carcinoma, wherein an elevated level of calreticulin compared with the level of calreticulin in a normal sample is indicative of an increased risk of urothelial carcinoma.

2. The method of claim 1 for detecting urothelial carcinoma comprising immunologically determining calreticulin protein in a urine sample by using an antibody that specifically binds with calreticulin protein or a fragment thereof.

3. The method of claim 1, wherein said tissue is bladder transitional cell carcinoma.

4. The method of claim 1, wherein the urothelial carcinoma is bladder carcinoma.

5. The method of claim 1, wherein the urothelial carcinoma is renal pelvic carcinoma.

* * * * *